US00PP16719P2

(12) United States Plant Patent
De Geus

(10) Patent No.: US PP16,719 P2
(45) Date of Patent: Jun. 27, 2006

(54) ROSE PLANT NAMED 'BOTA 2802'

(50) Latin Name: *Rosa hybrida*
Varietal Denomination: BOTA 2802

(76) Inventor: Jeroen De Geus, Strijp 9, 7891 XC Klazienaveen (NL)

( * ) Notice: Subject to any disclaimer, the term of this patent is extended or adjusted under 35 U.S.C. 154(b) by 61 days.

(21) Appl. No.: 11/022,008

(22) Filed: Dec. 24, 2004

(51) Int. Cl.
*A01H 5/00* (2006.01)

(52) U.S. Cl. ..... Plt./132

(58) Field of Classification Search ..... Plt./132, Plt./133, 130
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinctive cultivar of Hybrid Tea Rose plant named 'BOTA 2802', characterized by its strong and dark green-colored leaves; vigorous growth habit; long and strong flowering stems without thorns; pink, white and green-colored flowers with numerous petals; high yield of cut flowering stems; good postproduction longevity; and not susceptible to Powdery Mildew.

1 Drawing Sheet

Botanical designation: *Rosa hybrida.*
Cultivar denomination: 'BOTA 2802'.

BACKGROUND OF THE INVENTION

The present invention relates to a new and distinct cultivar of Hybrid Tea Rose plant, botanically known as *Rosa hybrida,* and hereinafter referred to by the cultivar name BOTA 2802.

The new cultivar is a product of a planned breeding program conducted by the Inventor in Klazienaveen, The Netherlands. The objective of the breeding program was to develop new cut Rose cultivars with a high yield of cut flowering stems, large flower buds and flowers, attractive flower color, long and strong stems, dark green leaves and good postproduction longevity.

The new cultivar originated from a cross-pollination made by the Inventor on Feb. 15, 2002 of the *Rosa hybrida* cultivar Iceberg, not patented, as the female, or seed, parent and the *Rosa hybrida* cultivar Passion, not patented, as the male, or pollen, parent. The cultivar BOTA 2802 was discovered and selected by the Inventor as a flowering plant within the progeny of the stated cross-pollination in a controlled environment in Klazienaveen, The Netherlands.

Asexual reproduction of the new cultivar by cuttings at Klazienaveen, The Netherlands, since June, 2002, has shown that the unique features of the new cultivar are stable and reproduced true to type in successive generations of asexual reproduction.

SUMMARY OF THE INVENTION

The following traits have been repeatedly observed and are determined to be the unique characteristics of 'BOTA 2802'. These characteristics in combination distinguish the new Hybrid Tea Rose as a new and distinct cultivar:

1. Strong and dark green-colored leaves.
2. Vigorous growth habit.
3. Long and strong flowering stems without thorns.

4. Pink, white and green-colored flowers with numerous petals.
5. High yield of cut flowering stems.
6. Good postproduction longevity.
7. Not susceptible to Powdery Mildew.

Plants of the new Hybrid Tea Rose can be compared to plants of the female parent, the cultivar Iceberg. In side-by-side comparisons conducted in Klazienaveen, The Netherlands, plants of the new Hybrid Tea Rose differed from plants of the cultivar Iceberg in the following characteristics:

1. Plants of the new Hybrid Tea Rose had longer flowering stems than plants of the cultivar Iceberg.
2. Plants of the new Hybrid Tea Rose produced fewer flowering stems than plants of the cultivar Iceberg.
3. Plants of the new Hybrid Tea Rose had broader flower buds than plants of the cultivar Iceberg.
4. Plants of the new Hybrid Tea Rose had more petals per flower than plants of the cultivar Iceberg.
5. Plants of the new Hybrid Tea Rose and the cultivar Iceberg differed in flower color as plants of the cultivar Iceberg had white-colored flowers.
6. Plants of the new Hybrid Tea Rose had better postproduction longevity than plants of the cultivar Iceberg.

Plants of the new Hybrid Tea Rose can be compared to plants of the male parent, the cultivar Passion. In side-by-side comparisons conducted in Klazienaveen, The Netherlands, plants of the new Hybrid Tea Rose differed from plants of the cultivar Passion in the following characteristics:

1. Plants of the new Hybrid Tea Rose had longer flowering stems than plants of the cultivar Passion.
2. Plants of the new Hybrid Tea Rose produced fewer flowering stems than plants of the cultivar Passion.
3. Plants of the new Hybrid Tea Rose had larger flower buds than plants of the cultivar Passion.
4. Plants of the new Hybrid Tea Rose and the cultivar Passion differed in flower color as plants of the cultivar Passion had red-colored flowers.

Plants of the new Hybrid Tea Rose can be compared to plants of the Rose cultivar Bella Vita, not patented. In side-by-side comparisons conducted in Klazienaveen, The Netherlands, plants of the new Hybrid Tea Rose differed from plants of the cultivar Bella Vita in the following characteristics:

1. Plants of the new Hybrid Tea Rose produced more flowering stems than plants of the cultivar Bella Vita.
2. Plants of the new Hybrid Tea Rose did not have any thorns whereas plants of the cultivar Bella Vita had thorns.
3. Plants of the new Hybrid Tea Rose had larger flower buds than plants of the cultivar Bella Vita.
4. Plants of the new Hybrid Tea Rose and the cultivar Bella Vita differed in flower color as plants of the cultivar Bella Vita had lighter pink-colored flowers and did not have green coloration on the outer petals.
5. Plants of the new Hybrid Tea Rose had better postproduction longevity than plants of the cultivar Bella Vita.
6. Plants of the new Hybrid Tea Rose were not susceptible to Powdery Mildew whereas plants of the cultivar Bella Vita were susceptible to Powdery Mildew.

Plants of the new Hybrid Tea Rose can be compared to plants of Rose cultivar Barcelona, not patented. In side-by-side comparisons conducted in Klazienaveen, The Netherlands, plants of the new Hybrid Tea Rose differed from plants of the cultivar Barcelona in the following characteristics:

1. Plants of the new Hybrid Tea Rose had longer flowering stems than plants of the cultivar Barcelona.
2. Plants of the new Hybrid Tea Rose had longer stipules than plants of the cultivar Barcelona.
3. Plants of the new Hybrid Tea Rose had larger flower buds than plants of the cultivar Barcelona.
4. Plants of the new Hybrid Tea Rose and the cultivar Barcelona differed in flower color as plants of the cultivar Barcelona had darker pink-colored flowers.

BRIEF DESCRIPTION OF PHOTOGRAPHS

The accompanying colored photographs illustrate the new Hybrid Tea Rose plant showing the colors as true as it is reasonably possible to obtain in colored reproductions of this type. Colors in the photographs may differ slightly from the color values cited in the detailed botanical description which accurately describe the actual colors of the new Hybrid Tea Rose.

The photograph at the top of the sheet comprises a side perspective view of a typical flowering stem of the new Hybrid Tea Rose.

The photograph at the bottom of the sheet comprises a close-up view of a typical flowering stem of the new Hybrid Tea Rose.

DETAILED BOTANICAL DESCRIPTION

Plants of the new Hybrid Tea Rose have not been observed under all possible environmental conditions. The phenotype may vary significantly with variations in environment such as temperature and light level without, however, any variance in genotype.

The aforementioned photographs, following observations and measurements describe plants grown in De Kwakel, The Netherlands during the summer and autumn, in glass-covered greenhouses with temperatures ranging from 19 to 25° C., night temperatures ranging from 15 to 19° C. and light levels averaging 7,000 lux. Plants used for the photographs and the description were about five months old. In the following description, color references are made to The Royal Horticultural Society Colour Chart, 1995 Edition, except where general terms of ordinary dictionary significance are used.

Classification:

*Botanical.*—*Rosa hybrida* cultivar BOTA 2802.

*Commercial.*—Hybrid Tea Rose used as a cut flower.

Parentage:

*Female, or seed, parent.*—*Rosa hybrida* cultivar Iceberg, not patented.

*Male, or pollen, parent.*—*Rosa hybrida* cultivar Passion, not patented.

Propagation:

*Type.*—By vegetative cuttings.

*Time to initiate roots, summer.*—About 12 days at 25° C.

*Time to initiate roots, winter.*—About 14 days at 20° C.

*Time to develop roots, summer.*—About 21 days at 25° C.

*Time to develop roots, winter.*—About 24 days at 20° C.

*Root description.*—Fine, fibrous; white in color.

*Rooting habit.*—Freely branching, dense.

Plant description:

*Form.*—Upright.

*Plant height.*—About 80 to 90 cm.

*Plant width.*—About 90 to 100 cm.

*Growth habit.*—Vigorous.

*Yield of flowering stems.*—In one year, about 200 flowering stems per square meter can be harvested per plant.

*Flowering stems.*—Quantity per plant: About 10 to 12 per plant. Aspect: Straight, upright. Strength: Strong. Length: About 80 to 90 cm. Diameter: About 2 cm. Internode length: About 5 to 6 cm. Texture: Glabrous. Color: 137A. Thorns: Thorns have not been observed.

*Foliage description.*—Arrangement: Alternate; compound with about three to seven leaflets. Quantity per flowering stem: About 13 compound leaves. Leaf length: About 11 to 15 cm. Leaf width: About 11 to 16 cm. Terminal leaflet length: About 8 to 11 cm. Terminal leaflet width: About 5 to 6 cm. Lateral leaflet length: About 6 to 8 cm. Lateral leaflet width: About 3 to 4 cm. Leaflet shape: Ovate. Leaflet apex: Broadly acute. Leaflet base: Cordate. Leaflet margin: Serrate. Leaflet texture, upper and lower surfaces: Smooth, glabrous; leathery. Leaflet venation pattern: Pinnate. Leaf petiole length: About 1.5 to 2.5 cm. Leaf petiole diameter: About 1 to 2 mm. Leaflet petiole length: About 1 to 3 cm. Leaflet petiole diameter: About 1 mm. Stipules: Length: About 2 cm. Diameter: About 8 mm. Shape: Roughly lanceolate. Apex: Cleft. Base: Cuneate. Texture, upper and lower surfaces: Smooth, glabrous; leathery. Color: Developing and fully expanded foliage, upper surface: 147A to darker than 147A. Developing and fully expanded foliage, lower surface: 147B. Venation, upper surface: 146B. Venation, lower surface: 146D. Leaf and leaflet petioles, upper and lower surfaces: 146B. Stipule, upper surface: 147A. Stipule, lower surface: 137A.

Flower description:

*Flower type and habit.*—Pink, white and green-colored flowers; symmetrical rosette flowers. Freely and recurrent flowering habit. Flowers arranged singly at terminal apices. Flowers persistent.

*Flowering season/time to flower.*—Year-round under greenhouse conditions.

*Flower diameter.*—About 7 to 8 cm.

*Flower depth (height).*—About 5 to 6 cm.

*Flower longevity on plant.*—About three weeks.

*Flower longevity as a cut flower.*—About two weeks.

*Fragrance.*—Slight, typical rose fragrance.

*Flower buds.*—Shape: Ovoid. Length: About 4 to 5 cm. Diameter: About 3 to 4 cm. Color: Close to 62D.

*Petals.*—Quantity: About 44 per flower arranged in numerous whorls. Length: About 4 to 6.5 cm. Width: About 4.5 to 6.5 cm. Shape: Obovate. Apex: Rounded. Margin: Entire. Texture, upper and lower surfaces: Smooth, satiny. Color: When opening, upper surface: 62D; towards the margins, 62A. When opening, lower surface: 62D; towards the margins, 66B. Fully opened, upper and lower surfaces: 159C; towards the margins, 58C to 58D; outside petals, tinged with 145B.

*Sepals.*—Quantity per flower: Five. Length: About 3.5 cm. Width: About 1.1 cm. Shape: Lanceolate. Apex: Apiculate. Base: Cuneate. Margin: Entire. Texture, upper and lower surfaces: Pubescent. Color: Upper surface: 147C. Lower surface: 144A.

*Peduncles.*—Strength: Strong. Aspect: Erect. Length: About 7 to 8 cm. Diameter: About 6 to 7 mm. Texture: Smooth, glabrous. Color: 144A.

*Reproductive organs.*—Stamens: Quantity per flower: About 150. Anther length: About 4 mm. Anther shape: Elliptic. Anther color: 163C. Filament color: 61C. Pistils: Quantity per flower: About 200. Pistil length: About 5 mm. Stigma shape: Elliptic. Stigma color: 152D. Style length: About 4 mm. Style color: 63B. Receptacle height: About 1 to 1.3 cm. Receptacle diameter: About 1.8 to 2.2 cm. Receptacle color: 145D.

*Seed/fruit.*—Seed and fruit development has not been observed.

Disease/pest resistance: Plants of the new Hybrid Tea Rose have not been observed to be susceptible to Powdery Mildew. Plants of the new Hybrid Tea Rose have not been observed to be resistant to pests and other pathogens common to Roses.

Temperature tolerance: Plants of the new Hybrid Tea Rose have been observed to tolerate temperatures from 12 to 32° C.

It is claimed:

1. A new and distinct Hybrid Tea Rose plant named 'BOTA 2802', as illustrated and described.

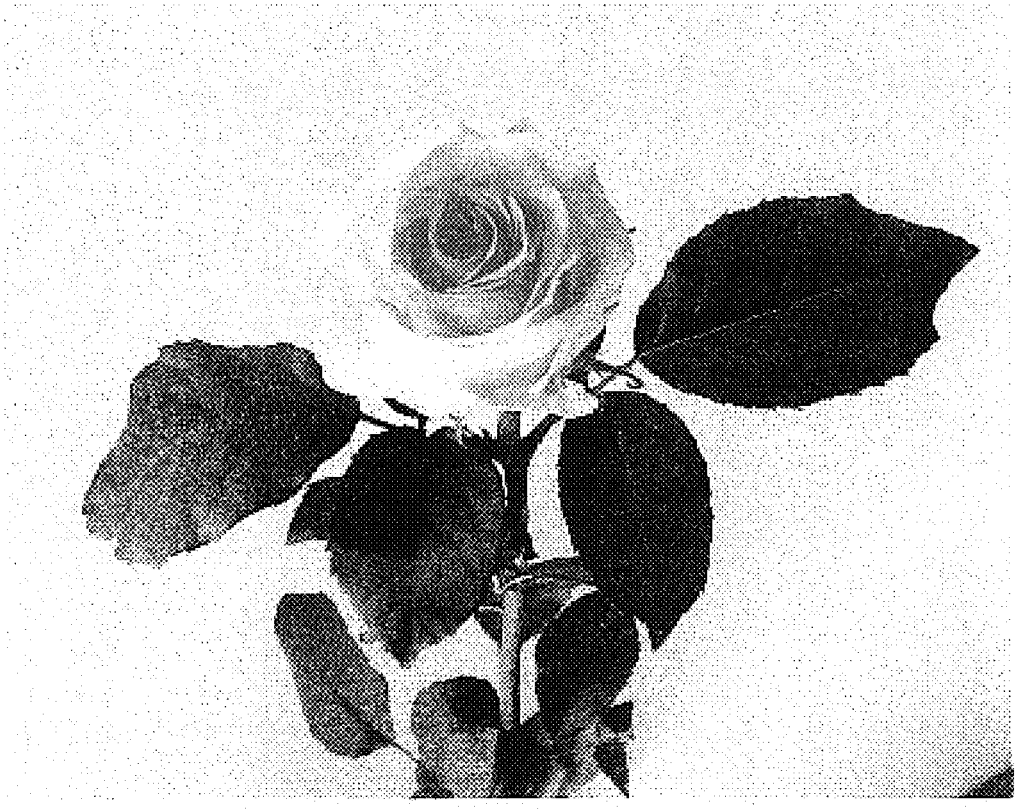
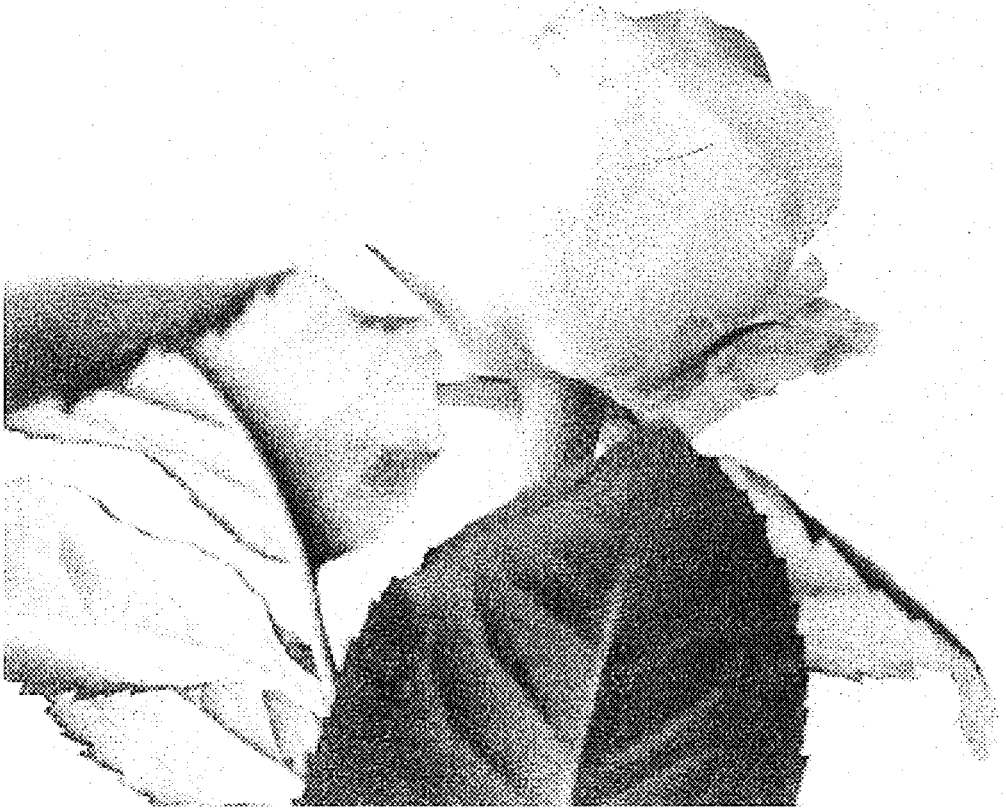

* * * * *